Figure 1:
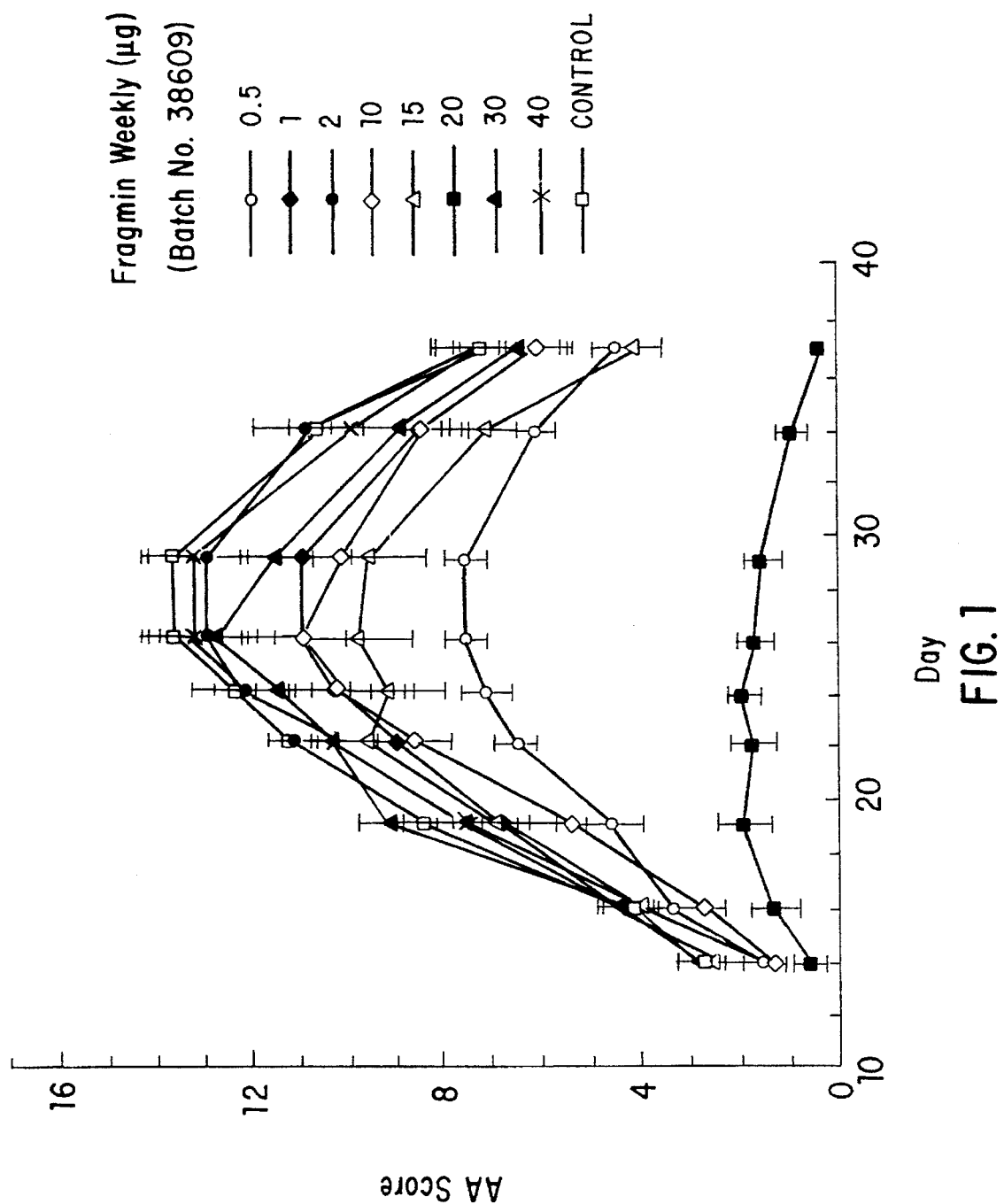

United States Patent [19]

Cohen et al.

[11] Patent Number: 5,474,987
[45] Date of Patent: Dec. 12, 1995

[54] METHODS OF USING LOW MOLECULAR WEIGHT HEPARINS TREATMENT OF PATHOLOGICAL PROCESSES

[75] Inventors: Irun R. Cohen; Ofer Lider; Rami Hershkoviz, Herzliya, all of Israel

[73] Assignee: Yeda Research and Development Co. Ltd., Israel

[21] Appl. No.: 384,203

[22] Filed: Feb. 3, 1995

Related U.S. Application Data

[63] Continuation of Ser. No. 878,188, May 1, 1992, abandoned.

[30] Foreign Application Priority Data

| May 2, 1991 | [IL] | Israel | 98028 |
| May 28, 1991 | [IL] | Israel | 98298 |

[51] Int. Cl.$^6$ .................................................. A61K 31/725
[52] U.S. Cl. .......................... 514/56; 514/54; 514/825; 536/21; 536/54; 536/55
[58] Field of Search .............................. 514/54, 56, 825; 536/21, 54, 55

[56] References Cited

U.S. PATENT DOCUMENTS

| 4,281,108 | 7/1981 | Fussi | 536/21 |
| 4,401,662 | 8/1983 | Lormeau et al. | 514/56 |
| 4,788,307 | 11/1988 | Lormeau et al. | 536/21 |
| 4,840,941 | 6/1989 | Ueno et al. | 514/59 |
| 4,973,580 | 11/1990 | Mascellani et al. | 514/54 |
| 4,990,502 | 2/1991 | Lormeau et al. | 514/56 |
| 5,039,529 | 8/1991 | Bergendal et al. | 424/63 |

FOREIGN PATENT DOCUMENTS

| 0259336 | 5/1963 | Australia . |
| 0114589A1 | 8/1984 | European Pat. Off. . |
| 0375976 | 7/1990 | European Pat. Off. . |
| 0394971 | 10/1990 | European Pat. Off. . |
| WO88/05301 | 7/1988 | WIPO . |
| WO90/01501 | 2/1990 | WIPO . |
| WO90/03791 | 4/1990 | WIPO . |

OTHER PUBLICATIONS

Ekre, H.-P. et al. *Advances in Experimental Medicine and Biology* 1992, 313: 329–340.
Berk, B. C. et al., *J. Am. Coll. Cardiol.* 1991, 17:111B–117B.
Gervasi, G. B. et al., *Arzneim.–Forsch./Drug. Res.* 1991, 41:410–413.
Beutler, B. and A. Cerami, *Ann. Rev. Immunol.* 1989, 7:625–655.
Boneu, B. et al., *Thrombosis Research* 1987 46:845.
Bratt, G. et al. *Thrombosis and Haemostasis* 1985, 53:208
Castano, L. and Eisenbarth, G. S. *Annu. Reb. Immunol* 1990 8:647–679.
Cohen, L. R. et al. *Arthritis and Rehumatism* 1985 28:841–845.
Colman, R. W. et al. *American Journal of Pathology* 1976 82(1):25–42.
Elias, D. et al. *Proc. Natl. Acad Sci., U.S.A.* 1990 87:1576–1580.
Goldberg, I. D. et al. *Annals of the New York Academy of Sciences* 1986 463:289–291.
Gospodarowicz, D. et al. *J. Biol. Chem.* 1978 253:3736–3743.
Holoshitz, Y. et al. *Science* 1983 219:56.
Horvath, J. E. et al. *Aust. N. Z. J. Med.* 1975 5(6):537–539.
Kiricuta, I. et al. *Physiology Chemistry and Physics* 1978 10:247–253.
Lider, O. et al. *Eur. J. Immunol.* 1990, 20:493–499.
Lider, O. et al. *J. Clin. Invest.* 1989 83:752–756.
Lindhardt, R. J. et al. *The Journal of Biological Chemistry* 1988 263(26):13090–13096.
Matsuyama, T. et al., *J. Viol.* 1989, 63(6):2504–2509.
Michihiko, S. et al. *Lancet* 1989, 1(8648):1206–1207.
Naparstek, Y. et al. *Nature* 1984 310:241–243.
Okamoto, T. et al. *Aids Rs. Hum. Retroviruses* 1989, 5(2):131–138.
Ono, K. and Linsay, E. S. *J. Thorax. Cardiovasc. Surg.* 1969 45:225–229.
Pearson, C. M. *Arthritis and Rheumatism* 1964 7:80.
Pearson, C. M., *Proc. Soc. Exp. Biol. Med.* 1956 91:95.
Sy, M. S. et al. *Cellular Immunology* 1983 82:23–32.
Toivonen, M. L. et al., Meth and Find Exptl. Clin. Pharmacol. 1982 4(6):359–363.
Wallach, D. *J. Immunology* 1984 132:2464–2469.
Westwick, J. et al. *Thrombosis Research* 1986 42:435–447.
Linhardt et al; J. Biol. Chem. 257(13):7310–7313 (1982).
Bergqvist et al; Thromb. Res. 32:381–391 (1983).
Larsen et al; J. Pharm. Exp. Ther. 231(2):373–378 (1984).
Redini et al; Biochem. Pharmacol. 37(22):4257–4261 (1988).
Wright, Jr. et al; J. Biol. Chem. 264(3):1534–1542 (1989).
Larsen et al; J. Biol. Chem. 264(3):1570–1577 (1989).
Mattsson et al; Ann. N.Y. Acad. Sci. 556:323–332 (1989).
Fareed et al; Ann. N.Y. Acad. Sci. 556:333–353 (1989).
Dillman et al. *Mol. Biother.* 1992, 4, 117–121.

*Primary Examiner*—Douglas W. Robinson
*Assistant Examiner*—Kathleen Kahler Fonda
*Attorney, Agent, or Firm*—Pennie & Edmonds

[57] ABSTRACT

The present invention relates to methods for the prevention and/or treatment of pathological processes involving the induction of TNF-α secretion comprising a pharmaceutically acceptable carrier and a low molecular weight heparin (LMWH). In the pharmaceutical compositions of the present invention, the LMWH is present in a low effective dose and is administered at intervals of about 5–8 days. Furthermore, the LMWH is capable of inhibiting in vitro TNF-α secretion by resting T cells and/or macrophages in response to T cell-specific antigens, mitogens, macrophage activators, disrupted extracellular matrix (dECM), laminin, fibronectin, and the like.

6 Claims, 8 Drawing Sheets

METHODS OF USING LOW MOLECULAR WEIGHT HEPARINS TREATMENT OF PATHOLOGICAL PROCESSES

This is a continuation of application Ser. No. 07/878,188, filed May 1, 1992, now abandoned.

1. FIELD OF THE INVENTION

The present invention relates to pharmaceutical compositions for the prevention and/or treatment of pathological processes involving induction of Tumor Necrosis Factor alpha (TNF-α) secretion, which comprise an effective low dosage of a low molecular weight heparin (LMWH) to be administered at intervals of between five to eight days.

The LMWHs to be used according to the invention have an average molecular weight of from about 3,000 to about 6,000 and inhibit TNF-α secretion by resting T cells and/or macrophages in vitro in response to activation by T cell-specific antigens, T cell mitogens, macrophage activators, disrupted extracellular matrix (dECM), fibronectin, laminin or other ECM components.

2. BACKGROUND OF THE INVENTION

TNF-α, a cytokine produced by monocytes (macrophages) and T lymphocytes, is a key element in the cascade of factors that produce the inflammatory response and has many pleiotropic effects as a major orchestrator of disease states (B. Beutler and A. Cerami, *Ann. Rev. Immunol.* (1989) 7:625–655).

The biologic effects of TNF-α depend on its concentration and site of production: at low concentrations, TNF-α may produce desirable homeostatic and defense functions, but at high concentrations, systemically or in certain tissues, TNF-α can synergize with other cytokines, notably interleukin-1 (IL-1) to aggravate many inflammatory responses.

The following activities have been shown to be induced by TNF-α (together with IL-1); fever, slow-wave sleep, hemodynamic shock, increased production of acute phase proteins, decreased production of albumin, activation of vascular endothelial cells, increased expression of major histocompatibility complex (MHC) molecules, decreased lipoprotein lipase, decreased cytochrome P450, decreased plasma zinc and iron, fibroblast proliferation, increased synovial cell collagenase, increased cyclo-oxygenase activity, activation of T cells and B cells, and induction of secretion of the cytokines, TNF-α itself, IL-1 and IL-6.

How TNF-α exerts its effects is not known in detail, but many of the effects are thought to be related to the ability of TNF-α to stimulate cells to produce prostaglandins and leukotrienes from arachidonic acid of the cell membrane.

TNF-α, as a result of its pleiotropic effects, has been implicated in a variety of pathologic states in many different organs of the body. In blood vessels, TNF-α promotes hemorrhagic shock, down regulates endothelial cell thrombomodulin and enhances a procoagulant activity. It causes the adhesion of white blood cells and probably of platelets to the walls of blood vessels, and so, may promote processes leading to atherosclerosis, as well as to vasculitis.

TNF-α activates blood cells and causes the adhesion of neutrophils, eosinophils, monocytes/macrophages and T and B lymphocytes. By inducing IL-6 and IL-8, TNF-α augments the chemotaxis of inflammatory cells and their penetration into tissues. Thus, TNF-α has a role in the tissue damage of autoimmune diseases, allergies and graft rejection.

TNF-α has also been called cachectin because it modulates the metabolic activities of adipocytes and contributes to the wasting and cachexia accompanying cancer, chronic infections, chronic heart failure, and chronic inflammation. TNF-α may also have a role in anorexia nervosa by inhibiting appetite while enhancing wasting of fatty tissue.

TNF-α has metabolic effects on skeletal and cardiac muscle. It has also marked effects on the liver: it depresses albumin and cytochrome P450 metabolism and increases production of fibrinogen, α1-acid glycoprotein and other acute phase proteins. It can also cause necrosis of the bowel.

In the central nervous system, TNF-α crosses the blood-brain barrier and induces fever, increased sleep and anorexia. Increased TNF-α concentration is associated with multiple sclerosis. It further causes adrenal hemorrhage and affects production of steroid hormones, enhances collagenase and PGE-2 in the skin, and causes the breakdown of bone and cartilage by activating osteoclasts.

In short, TNF-α is involved in the pathogenesis of many undesirable inflammatory conditions in autoimmune diseases, graft rejection, vasculitis and atherosclerosis. It may have roles in heart failure, in the response to cancer and in anorexia nervosa. For these reasons, ways have been sought to regulate the secretion of TNF-α as a means to control a variety of diseases.

The prime function of the immune system is to protect the individual against infection by foreign invaders such as microorganisms. It may, however, also attack the individual's own tissues leading to pathologic states known as autoimmune diseases. The aggressive reactions of an individual's immune system against tissues from other individuals are the reasons behind the unwanted rejections of transplanted organs. Hyper-reactivity of the system against foreign substances causes allergy giving symptoms like asthma, rhinitis and eczema.

The cells mastering these reactions are the lymphocytes, primarily the activated T lymphocytes, and the pathologic inflammatory response they direct depends on their ability to traffic through blood vessel walls to and from their target tissue. Thus, reducing the ability of lymphocytes to adhere to and penetrate through the walls of blood vessels may prevent autoimmune attack, graft rejection and allergy. This would represent a new therapeutic principle likely to result in better efficacy and reduced adverse reactions compared to the therapies used today.

Atherosclerosis and vasculitis are chronic and acute examples of pathological vessel inflammation. Atherosclerosis involves thickening and rigidity of the intima of the arteries leading to coronary diseases, myocardial infarction, cerebral infarction and peripheral vascular diseases, and represents a major cause of morbidity and mortality in the Western world. Pathologically, atherosclerosis develops slowly and chronically as a lesion caused by fatty and calcareous deposits. The proliferation of fibrous tissues leads ultimately to an acute condition producing sudden occlusion of the lumen of the blood vessel.

TNF-α has been shown to facilitate and augment human immunodeficiency virus (HIV) replication in vitro (Matsuyama, T. et al., *J. Virol.* (1989) 63(6):2504–2509; Michihiko, S. et al., *Lancet* (1989) 1(8648):1206–1207) and to stimulate HIV-1 gene expression, thus, probably triggering the development of clinical AIDS in individuals latently infected with HIV-1 (Okamoto, T. et al., *AIDS Res. Hum. Retroviruses* (1989) 5(2):131–138).

Heparin is a glycosaminoglycan, a polyanionic sulfated polysaccharide, which is used clinically to prevent blood clotting as an antithrombotic agent. In animal, models heparin has been shown to reduce the ability of autoimmune T lymphocytes to reach their target organ (Lider, O. et al., *Eur. J. Immunol.* (1990) 20:493–499). Heparin was also shown to suppress experimental autoimmune diseases in rats and to prolong the allograft survival in a model of skin transplantation in mice, when used in low doses (5 μg for mice and 20 μg for rats) injected once a day (Lider, O. et al., *J. Clin. Invest.* (1989) 83:752–756).

The mechanisms behind the observed effects are thought to involve inhibition of release by T lymphocytes of enzyme(s) necessary for penetration of the vessel wall, primarily the enzyme heparanase that specifically attacks the glycosaminoglycan moiety of the sub-endothelial extracellular matrix (ECM) that lines blood vessels (Naparstek, Y. et al., *Nature* (1984) 310:241–243). Expression of the heparanase enzyme is associated with the ability of autoimmune T lymphocytes to penetrate blood vessel walls and to attack the brain in the model disease experimental autoimmune encephalomyelitis (EAE).

European Patent Application EP 0114589 (Folkman et al.) describes a composition for inhibition of angiogenesis in mammals in which the active agents consist essentially of (1) heparin or a heparin fragment which is a hexasaccharide or larger and (2) cortisone or hydrocortisone or the 11-α isomer of hydrocortisone. According to the disclosure, heparin by itself or cortisone by itself are ineffective; only the combination of both gives the desired effects. Although there is no proof in the literature that there is a connection between angiogenesis and autoimmune diseases, the description on page 5 of the patent application connects angiogenesis with psoriasis and with arthritis, indicating the use of high doses of 25,000 units to 47,000 units of heparin per day.

Horvath, J.E. et al., *Aust. N.Z.J. Med.* (1975) 5(6):537–539 describe the effect of subanticoagulant doses of subcutaneous heparin on early renal allograft function. The daily dosage is high (5000 U) and the conclusion of the study is that heparin in subanticoagulant doses has no effect on early graft function or graft survival and that it may be associated with increased hemorrhagic complications.

Toivanen, M.L. et al., *Meth. and Find. Exp. Clin. Pharmacol.* (1982) 4(6):359–363, examined the effect of heparin in high dosage (1000 U/rat) in the inhibition of adjuvant arthritis in rats and found that heparin enhanced the severity of the rat adjuvant arthritis.

PCT Patent: Application PCT/AU88/00017 published under No. WO88/05301 (Parish et al.) describes sulphated polysaccharides that block or inhibit endoglycosylase activity, such as heparanase activity, for use as antimetastatic and anti-inflammatory agents. Heparin and heparin derivatives, such as periodate oxidized, reduced heparins, that had negligible anticoagulant activity, were shown to have antimetastatic and anti-inflammatory activity when used in dosages within, the range of 1.6–6.6 mg per rat daily, administered by constant infusion (corresponding to 75–308 mg daily for an adult human patient).

3. SUMMARY OF THE INVENTION

The present invention is related to pharmaceutical compositions for the prevention and/or treatment of pathological processes involving the induction of TNF-α secretion comprising a pharmaceutically acceptable carrier and a low molecular weight heparin (LMWH) present in a low effective dose for administration at intervals of about 5–8 days and which LMWH is capable of inhibiting in vitro TNF-α secretion by resting T cells and/or macrophages in response to T cell-specific antigens, mitogens, macrophage activators, disrupted extracellular matrix (dECM), laminin, fibronectin, or other ECM components.

In a particular embodiment of the present invention the LMWH of the pharmaceutical composition has an average molecular weight of from about 3,000 to about 6,000 and, furthermore, may be administered every fifth or seventh day.

It is also an objective of the present invention to provide pharmaceutical compositions to be administered at intervals of about 5–8 days for the prevention and/or treatment of pathological processes involving the induction of TNF-α secretion comprising a pharmaceutically acceptable carrier and a low molecular weight heparin (LMWH) present in a low effective dose and which LMWH is capable of inhibiting experimental delayed type hypersensitivity (DTH) reactions to an applied antigen as evidenced by a reduction in the induration observed after the application of the antigen to the skin five to seven days after the administration of the pharmaceutical composition relative to the induration observed after the application of the antigen to the skin in the absence of or after recovery from the administration of the pharmaceutical composition. Examples of the applied antigen include, but are not limited to, tetanus, myelin basic protein, purified protein derivative, oxazolone, and the like.

Furthermore, it is an objective of the present invention to provide pharmaceutical compositions that may be administered in any manner as dictated by the particular application at hand including, but not limited to, enteral administration (including oral) or parenteral administration (including topical or inhalation with the aid of aerosols). In preferred embodiments, the pharmaceutical compositions of the present invention are administered subcutaneously or intravenously.

Thus, the present invention is useful, for example, in delaying or preventing allograft rejection and treating or preventing a variety of pathological processes such as those related to autoimmune diseases, allergy, inflammatory diseases (in particular, inflammatory bowel disease), or acquired immunodeficiency syndrome (AIDS). The present invention also finds utility in the treatment of diabetes type I, periodontal disease, uveitis, rheumatic diseases (in particular, rheumatoid arthritis), atherosclerosis, vasculitis, or multiple sclerosis.

The pharmaceutical compositions of the present invention contain low effective doses of the prescribed LMWH and typically contain a single low dose unit of less than 5 mg of LMWH, preferably from about 0.3 to about 3 mg, and most preferably contain a single low dose unit of from 1 to 1.5 mg.

The present invention also contemplates broadly a method of using a low molecular weight heparin (LMWH) which is capable of inhibiting in vitro TNF-α secretion by resting T cells and/or macrophages in response to T cell-specific antigens, mitogens, macrophage activators, disrupted extracellular matrix (dECM), laminin, fibronectin, or other ECM components for the preparation of a pharmaceutical composition to be administered at intervals of about 5–8 days for the prevention and/or treatment of pathological processes involving induction of TNF-α secretion which method comprises combining a low effective dose of the LMWH with a pharmaceutically acceptable carrier.

A still further object of the present invention is to provide a method of treating a subject suffering from a pathological process involving induction of TNF-α secretion comprising administering to such subject a pharmaceutical composition, as described above, at intervals of about 5–8 days.

Further objects of the present invention will become apparent to those skilled in the art upon further review of the following disclosure, including the detailed descriptions of specific embodiments of the invention.

4. DETAILED DESCRIPTION OF THE INVENTION

According to the present invention, it was found that treatment with low molecular weight heparins (LMWHs) inhibited the ability of T cells and macrophages to secrete TNF-α. The functional expression of this effect can be seen in the inhibition in mice and humans of the delayed type hypersensitivity (DTH) reaction, an inflammatory reaction triggered by cells involving macrophages and other inflammatory cells. Treatment with LMWHs at doses affecting TNF-α production also was able to inhibit a model of autoimmune arthritis called adjuvant arthritis (AA). LMWH treatment also prolonged the survival of allogeneic heart transplants in rats and abrogated insulin dependent diabetes mellitus (IDDM) in NOD mice. Moreover, treatment with LMWHs prevented the induction of TNF-α production by T cells and macrophages in response to the stimulus of damaged subendothelial extracellular matrix (ECM). Since TNF-α at the site of vascular injury has probably a role in the process of atherosclerosis, inhibition of TNF-α at the site of damaged subendothelial ECM will ameliorate the pathogenic process of atherosclerosis. A most surprising aspect of treatment with LMWHs is that such treatment is most effective when administered at low doses at weekly intervals. High doses of LMWHs or doses of LMWHs given daily are not effective in inhibiting TNF-α secretion or immune reactions.

Low molecular weight heparins, produced by fractionation or controlled depolymerization of heparins, show improved antithrombotic performance but also different pharmacokinetic properties as compared to heparin: the half-life is doubled and the bioavailability is higher with respect to their, anticoagulant effect after subcutaneous injection (Bratt, G. et al. *Thrombosis and Haemostasis* (1985) 53:208; Bone, B. et al., *Thrombosis Research* (1987) 46:845).

According to the present invention it has now been found that LMWHs administered at subanticoagulant doses at several day intervals are effective in the prevention and/or treatment of pathological processes involving induction of TNF-α.

The LMWHs to be used according to the invention are derived from LMWHs with an average molecular weight of 3000–6000, such as, for example the LMWHs disclosed in European Patent EP 0014184. Some LMWHs are commercially available under different trade names, e.g., Fragmin®, Fraxiparin®, Fraxiparine®, Lovenox®/Clexane®.

LMWHs can be produced in several different ways: enrichment by fractionation by ethanol and/or molecular sieving, e.g., gel filtration or membrane filtration of the LMWH present in standard heparin and controlled chemical (by nitrous acid, β-elimination or periodate oxidation) or enzymatic (by heparinases) depolymerization. The conditions for depolymerization can be carefully controlled to yield products of desired molecular weights. Nitrous acid depolymerization is commonly used. Also employed is depolymerization of the benzylic ester of heparin by β-elimination, which yields the same type of fragments as enzymatic depolymerization using heparinases. LMWH with low anticoagulant activity and retaining basic chemical structure can be prepared by depolymerization using periodate oxidation or by removing the antithrombin-binding fraction of LMWH, prepared by other methods, using immobilized antithrombin for adsorption.

Fragmin® is a low molecular weight heparin with average molecular weight within the range of 4000–6000 dalton, produced by controlled nitrous acid depolymerization of sodium heparin from porcine intestinal mucosa. It is manufactured by Kabi Pharmacia, Sweden, under the name Fragmin®, for use as an antithrombotic agent as saline solutions for injection in single dose syringes of 2500 IU/0.2 ml and 5000 IU/0.2 ml, corresponding to about 16 mg and 32 mg, respectively.

Fraxiparin®, and Fraxiparine® are LMWHs with average molecular weight of approximately 4500 dalton, produced by fractionation or controlled nitrous acid depolymerization, respectively, of calcium heparin from porcine intestinal mucosa. It is manufactured by Sanofi (Choay Laboratories) for use as an antithrombotic agent in single doses comprising ca. 36 mg, corresponding to 3075 IU/0.3 ml of water.

Lovenox® (Enoxaparin/e), a LMWH fragment produced by depolymerization of sodium heparin from porcine intestinal mucosa, using β-elimination, is manufactured by Pharmuka SF, France and distributed by Rhone-Poulenc under the names Clexane® and Lovenox® for use as antithrombotic agent in single dose syringes comprising 20 mg/0.2 ml and 40 mg/0.4 ml of water.

As shown in the present application, the novel properties of LMWHs described are a common feature of all, LMWHs regardless of the manufacturing process, the structural differences (created by depolymerization or those dependent on variation in the heparin used as raw material) or the anticoagulant activity, provided the LMWH employed is capable of inhibiting TNF-e secretion in vitro by resting T cells and/or macrophages in response to activation by contact with specific antigens, mitogens, disrupted ECM or its protein components, such as fibronectin or laminin.

Another test useful to identify the LMWHs that are effective for the purpose of the present invention is the inhibition of experimental delayed type hypersensitivity (DTH) skin reactions, a T lymphocyte dependent reaction, to a variety of antigens (for example, tetanus antigen, myelin basic protein (MBP), purified protein derivative (PPD), and oxazolone). The LMWHs also inhibit T cell adhesion to ECM and its protein components.

The LMWHs effective according to the invention are incorporated into pharmaceutical compositions, for example, as water solutions, possibly comprising sodium chloride, stabilizers and other suitable non-active ingredients. The preferable way of administration is by injection, subcutaneous or intravenous, but any other suitable mode of administration is encompassed by the invention.

According to the invention, the LMWH is to be administered at intervals of five to eight days, preferably once a week.

The disorders that can be prevented or treated according to the invention are all disorders linked in pathological processes involving induction of TNF-α secretion, including atherosclerosis and vasculitis and pathological processes related thereto; autoimmune diseases, e.g., rheumatoid arthritis, diabetes type I (IDDM); allergy; graft rejection; acute and chronic inflammatory diseases, e.g. uveitis, bowel inflammation; anorexia nervosa; hemorrhagic shock caused by septicemia, and opportunistic infections in AIDS—immunocompromised individuals. In AIDS, the LMWHs will suppress replication of HIV and/or enhance resistance against the opportunistic infections, thereby preventing the development of AIDS-related complex (ARC).

It was observed according to the present invention that LMWHs can have a narrow dose range of effectiveness, and that different preparations of LMWHs can show different optimal biological effects. Therefore, it was necessary to establish a Unit Dose for LMWH preparation to be used according to the invention, said unit dose being based on a bioassay of inhibition of TNF-α secretion by mouse spleen cells from mice treated with LMWH or by inhibition of DTH reactivity by the LMWH. It was found that the ability of a particular dose of LMWH to inhibit TNF-α secretion is positively correlated with its ability to inhibit the delayed type hypersensitivity (DTH) reaction. This, cell-mediated inflammatory reaction in vivo is important because it is an expression of the processes involved in autoimmune diseases, graft rejection, some types of blood vessel inflammation and allergy.

It was thus established according to the invention that the lowest dose of LMWH per kg causing inhibition of TNF-α, production or inhibition of DTH reactivity by at least 50% is considered to constitute 12 mouse inhibitory units per kg (12 μ/kg). Because of the differences in surface area and metabolism between mice and humans, humans should be treated with a lower dose of LMWH, and 12 μ/kg in mouse is established to correspond to 1 μ/kg in humans. For example, the dose of Fragmin® batch 38609 effective in inhibiting both TNF-α secretion and DTH reactivity is 5 μg per mouse administered weekly. Since each mouse weighs about 25 g, the dose of Fragmin® 38609 equivalent to 12 μ/kg is 200 μg/kg of mice. The dose of 1 μ/kg suitable for humans is therefore 200 μg/kg: 12=16.67 μg/kg. A human weighing about 70 kg would then be treated by a dose of about 1.2 mg given in a single dose subcutaneously once every 7 days. Since individual humans vary biologically, the optimal dose may be different from about 1.2 mg and will lie below 5 mg, particularly within the range of 0.3 to 3 mg.

The dose of LMWH that should be effective in rats can be derived from the fact that the dose of LMWH per kg of rats is one-half the dose per kg of mice, i.e. 6 μ/kg. For example, if 12 u of Fragmin® batch 38609 is 200 μg/kg, then the 6 u dose suitable for rats should be 100 μg/kg or 20 μg per 200 g rat, administered once a week.

The invention will now be illustrated by the following non-limiting examples.

5. EXAMPLES

5.1. Example 1: Bioassay of Inhibition of TNF-α Secretion

Supernatants of spleen cells cultured in the presence or absence of LMWH, or spleen cells obtained from mice treated or untreated with LMWH in vivo are analyzed for their ability to secrete TNF-α. The TNF-α bioassay is based on the cytotoxic effect of TNF-α on cycloheximide (CHI)-sensitized cells and its quantitation by the neutral red uptake assay as described by Wallach D., *J. Immunology* (1984) 132:2464–2469. Briefly, the killing of CHI-sensitized HeLa cells by TNF-α present in the supernatants of the cells is measured, the concentration of TNF-α in said supernatants being determined by comparison to titration curves of TNF-α exogenously added. Cell viability is determined by incubation with neutral red for two hours, washing away excess dye, extracting the neutral red that was taken up by the cells with Sorenson's citrate buffer-ethanol mixture, and quantitating it colorimetrically at 570 nm with a Microelisa Autoreader.

Cells from mice treated with LMWH are obtained as follows: female mice of the BALB/c strain (25 grams, 2 months old), at least 5 mice per group, are injected subcutaneously with various doses of LMWH, usually in the range of 0.5 to 20 μg per mouse. Five days later the mice are killed by cervical dislocation, the spleens are removed and suspensions of spleen cells, depleted of red blood cells, are assayed for the production of TNF-α in response to induction by dECM, Concanavalin A (Con A) or lipopolysaccharide (LPS).

5.2. EXAMPLE 2: Bioassay of Inhibition of DTH Reactivity

Groups of mice are sensitized on the shaved abdominal skin with 100 μl of 3% oxazolone (OX) in acetone/olive oil (4:1, v:v). DTH sensitivity is elicited 5 days later as follows: mice are challenged with 20 μl of 0.5% OX (10 μl to each side of the ear) in acetone/olive oil. A constant area of the ear is measured immediately before challenge and 24 and 48 h later with a Mitutoyo engineer's micrometer. The individual measuring ear swelling is blinded to the identity of the groups of mice. The increment (Δ) of ear swelling is expressed as the mean in units of $10^{-2}$ mm or $10^{-4}$ inch (±SE) depending on the micrometer that is used. Percent inhibition is calculated as follows:

$$\% \text{ Inhibition} = \frac{\text{Positive control} - \text{experimental group}}{\text{Positive control} - \text{negative control}} \times 100$$

Mice are treated with LMWH as in Example 1, injected the day before primary sensitization to OX. On the fifth day after sensitization to OX, the mice are challenged to induce a DTH reaction, as described above.

The positive control is the DTH reaction elicited in immunized mice in the absence of treatment with LMWH. The negative control is the background swelling produced by the antigen in immunized mice.

5.3. EXAMPLE 3: Induction of TNF-α Secretion by T Cells and Macrophages In vitro Microtiter plates were prepared as follows: fibronectin (FN) or laminin (LN) (Sigma) were added to flat bottom 96-well plates (Costar) at a concentration of 1 μg/50 μl PBS per well and removed after 16 h. Remaining binding sites were blocked with BSA/PBS (10 mg/ml) which was added to the wells for 2 h and washed out. ECM-coated wells were prepared as follows: bovine corneal endothelial cells were cultured in flat bottom 96-well plates. The confluent layers of endothelial cells were dissolved and the ECM was left intact free of cellular debris (Gospodarowicz, D. et al. *J. Biol. Chem.* (1978) 253:3736). Disrupted ECM (dECM) was prepared by gently scratching the ECM three times with a 27G syringe needle and the exposed sites were subsequently coated with BSA/PBS. Resting cloned rat CD4$^+$ T cells, designated K1, which recognize myelin basic protein (MBP), were propagated and maintained in culture and were added to the wells, $10^5$ cells per well with or without $3 \times 10^5$ syngeneic splenic macrophages, in 100 μl per well RPMI 1640 (Gibco) supplemented with 1% BSA and antibiotics. The splenic macrophages were purified by removing the T and B cells using specific monoclonal antibodies (mAb). Where indicated, anti-murine TNF-α mAb (Genzyme, diluted 1/300) were added to the wells. MBP (100 μg/ml), Con A (2.5 μg/ml), LPS (1 μg/ml) were added to the wells where indicated. The plates were incubated at 37° C. in a humidified incubator for 3 h. Subsequently, the contents of the wells (4 wells per experimental group) were collected, centrifuged, and the media were assayed for TNF-α secretion as in Example 1: supernatants of cultured macrophages and lymphocytes were added to cultures of HeLa cells, which are sensitive to killing by TNF-α, and death of these cells in the presence of the test media was calibrated in comparison to titration curves of exogenous added TNF-α. Cell death is examined by the release of neutral red dye from the preincubated HeLa cells. The results shown here represent data obtained from a total of six experiments that produced essentially similar results.

Table 1 shows that T cells and macrophages cultured together can be induced to secrete TNF-α by contact with specific antigen MBP (group 4), the mitogen Con A (group 6) or LPS (group 8). However, in the absence of antigenic or mitogenic stimulus, TNF-α was also induced to be secreted by disrupted extracellular matrix (dECM; group 10) or by the ECM components fibronectin (FN; group 12) or laminin (LN group 14). Intact ECM was a weak inducer of TNF-α (group 16).

TABLE 1

TNF-α secretion by T cells and macrophages is induced by specific antigen MBP, Con A, LPS or dECM components.

| Group | TNF-α inducer | K1 cells cultured together with (yes) or without (no) macrophages | Secreted TNF-α (pg/ml) |
|---|---|---|---|
| 1 | none | no | 50 |
| 2 |  | yes | 65 |
| 3 | MBP antigen | no | 30 |
| 4 |  | yes | 950 |
| 5 | Con A | no | 120 |
| 6 |  | yes | 1300 |
| 7 | LPS | no | 50 |
| 8 |  | yes | 1500 |
| 9 | dECM | no | 30 |
| 10 |  | yes | 900 |
| 11 | FN | no | 20 |
| 12 |  | yes | 650 |
| 13 | LN | no | 50 |
| 14 |  | yes | 500 |
| 15 | ECM | no | 30 |
| 16 |  | yes | 120 |

5.4. EXAMPLE 4: Regulation of TNF-α Secretion by LMWHs

T cell and accessory cell cultures were prepared as described in Example 3. LMWH was added to the wells at the beginning of the cell culture. The levels of TNF-α were examined after 3 h of incubation.

Table 2 shows that the presence of LMWH (Fragmin® batch 38609) in vitro inhibited the induction of TNF-α secretion induced by specific antigen (MBP; group 4), mitogens (Con A and LPS; groups 6 and 8), dECM or ECM components (groups 10, 12 and 14). Since TNF-α secretion induced by dECM is likely to be involved in atherosclerosis, inhibition of TNF-α by LMWH will be beneficial in atherosclerosis.

TABLE 2

Induction of TNF-α secretion induced in vitro is inhibited by LMWH (Fragmin® batch 38609).

| Group | TNF-α Inducer | LMWH (1 μg/ml) | Secretion of TNF-α by cultures of T cells and macrophages (pg/ml) |
|---|---|---|---|
| 1 | none | none | 65 |
| 2 |  | yes | 30 |
| 3 | MPB antigen | none | 950 |
| 4 |  | yes | 60 |
| 5 | Con A | none | 1300 |
| 6 |  | yes | 80 |
| 7 | LPS | none | 1500 |
| 8 |  | yes | 80 |
| 9 | dECM | none | 900 |
| 10 |  | yes | 90 |
| 11 | FN | none | 650 |
| 12 |  | yes | 90 |
| 13 | LN | none | 500 |
| 14 |  | none | 70 |

5.5. EXAMPLE 5

To examine the effect of LMWH administered to mice in vivo on the secretion of TNF-α by spleen cells in vitro, the following experiment was conducted. BALB/c mice, 5 per group, were treated with various doses of LMWH (Fragmin® batch 38609) diluted in saline, injected subcutaneously. After one week, the animals were killed and their spleen cells, devoid of red blood cells, were examined for their ability to secrete TNF-α in response to control wells without dECM (A) or to wells coated with dECM (B). Measuring the levels of TNF-α secretion was done as described in Example 1. Table 3 shows the results which indicate that an injection of 5 μg of LMWH given once, 7 days earlier, inhibited TNF-α secretion induced by dECM. Higher or lower doses of LMWH were less effective. Thus, an optimal dose of LMWH administered in vivo a week earlier was effective.

TABLE 3

Ex vivo inhibition of T cell mediated TNF-α secretion in response to damaged ECM.

| LMWH treatment of BALB/c mice (weekly) | In vitro TNF-α secretion (pg/ml) by spleen cells cultured on: | | |
|---|---|---|---|
| | A. None | B. Damaged ECM | (% Inhibition) |
| 1 None | 30 | 400 | |
| 2 0.5 μg | 50 | 380 | (5) |
| 3 1 μg | 25 | 90 | (78) |
| 4 5 μg | 25 | 60 | (85) |
| 5 10 μg | 30 | 140 | (65) |
| 6 20 μg | 40 | 320 | (20) |

Table 4 shows that a 5 μg dose in vivo of the LMWH Fragmin® batch 38609 was also effective in inhibiting TNF-α secretion induced by LPS. BALB/c (4 mice per experimental group) mice were treated with the indicated amounts of LMWH diluted in saline and injected subcutaneously. After one week, the mice were injected intraperitoneally with 10 mg LPS, killed hours later and their spleen cells, devoid of red blood cells, were subsequently cultured in dECM coated wells for 3 hours in a humidified incubator. The levels of TNF-α secreted in response to the dECM was measured in the supernatants of the cultures. The results are given in Table 4.

TABLE 4

Treatment of mice with LMWH inhibits LPS mediated secretion of TNF-α by macrophages.

| LMWH treatment of mice (µg) | In vitro TNF-α secretion by macrophages (pg/ml) in response to LPS | % Inhibition |
|---|---|---|
| 0 | 690 | — |
| 0.1 | 500 | 28 |
| 1 | 350 | 50 |
| 5 | 120 | 82 |
| 20 | 550 | 20 |

5.6. EXAMPLE 6

To examine the effect of different LMWHs on the inhibition of TNF-α secretion and on DTH responses, mice were treated with the indicated LMWH administered subcutaneously in different concentrations. After one week, some of the mice were killed and the induction of TNF-α secretion in response to Con A activation in vitro was measured. The remaining mice were examined for their ability to respond to the antigen oxazolone. The results are expressed in Table 5 as percent inhibition compared to the responses of the LMWH untreated mice.

Two conclusions can be made by inspecting the results shown in Table 5:

1. Different batches of LMWH, each calibrated for by similar antithrombotic effect (factor X assay) have different optimal doses for inhibition of TNF-α secretion. Moreover, there are preparations of LMWH, such as Clexane® batch 4096, which have no inhibitory effect on TNF-α, secretion at any of the doses tried. Therefore, it may be concluded that the antithrombotic effect of a LMWH preparation is not related to the potential of the LMWH preparation for inhibition of TNF-α secretion. The two different bioassays are mediated by different factors present in the preparations.

2. The ability of a particular dose of LMWH to inhibit TNF-α secretion is positively correlated with its ability to inhibit DTH reaction, and the dose of a LMWH preparation optimally effective in inhibiting TNF-α secretion is also optimally effective in inhibiting the DTH reaction.

TABLE 5

Treatment of mice with different LMWHs inhibits both ex vivo TNF-α secretion and DTH responses.

| Weekly treatment of mice with LMWH | Conc: µg/mouse | Ex vivo Con A induced TNF-α secretion | | DTH responses | |
|---|---|---|---|---|---|
| | | pg/ml | % Inhibition | DTH | % Inhibition |
| Fragmin® | | | | | |
| Batch 38609 | None | 450 | — | 25 | — |
| | 0.5 | 425 | 5 | 21 | 12 |
| | 1 | 400 | 12 | 23 | 10 |
| | 5 | 68 | 85 | 6 | 73 |
| | 10 | 350 | 22 | 20 | 20 |
| | 50 | 435 | 8 | 26 | 0 |
| Batch 45389 | None | 320 | — | 28 | — |
| | 0.1 | 280 | 13 | 26 | 6 |
| | 1 | 70 | 78 | 4 | 89 |
| | 5 | 260 | 18 | 24 | 13 |
| | 10 | 290 | 10 | 26 | 6 |
| | 50 | 310 | 4 | 29 | 0 |
| Clexane® | | | | | |
| Batch 2088 | None | 400 | — | 22 | — |
| | 0.1 | 360 | 10 | 17 | 23 |
| | 1 | 64 | 84 | 3 | 87 |
| | 5 | 152 | 38 | 13 | 41 |
| | 10 | 380 | 4 | 23 | 0 |
| Batch 2066 | None | 350 | — | 23 | — |
| | 0.1 | 338 | 6 | 20 | 13 |
| | 1 | 185 | 54 | 8 | 65 |
| | 5 | 192 | 57 | 7 | 70 |
| | 10 | 186 | 55 | 7 | 70 |
| Batch 4096 | None | 320 | — | 24 | 0 |
| | 1 | 335 | 0 | 27 | 0 |
| | 5 | 325 | 0 | 26 | 0 |
| | 10 | 330 | 0 | 24 | 0 |

5.7. EXAMPLE 7: Treatment of Adjuvant Arthritis (AA) in Rats with Low Doses of LMWHs Adjuvant arthritis is an experimental disease inducible in some strains of rats by immunizing them to antigens of Mycobacterium tuberculosis (Pearson, C.M., Proc. Soc. Exp. Biolo Med. (1956) 91:91). This experimental disease is considered to be a model of human rheumatoid arthritis (Pearson, C.M., Arthritis Rheum. (1964) 7:80). The arthritis appears to be caused by T lymphocytes that recognize an antigen of M. tuberculosis that is cross-reactive with structures in the joint tissues (Cohen, I.R., et al., Arthritis Rheum. (1985) 28:841).

Lewis rats were immunized with M. tuberculosis (1 mg) in oil to induce adjuvant arthritis (Pearson, C.M., Proc. Soc. Exp. Biol. Med. (1956) 91:91). Five days later the rats were inoculated subcutaneously as indicated with the doses of LMWH and/or heparin and scored for the development of arthritis on a scale of 0–16 as described (Holoshitz, Y., et al., Science (1983) 219:56). All the experiments were performed with Fragmin®, Batch 38609.

In order to study the dose response to Fragmin® (FIG. 1) rats immunized to induce AA were injected subcutaneously weekly, starting on the 5th day after injection with 0.5 µg (o), 1 µg (♦), 2 µg (●), 10 µg (◊), 15 µg (Δ) 20 µg (■); 30 µg (▲), 40 µg (x) and PBS control (58 ). The dose was maximally effective in inhibiting arthritis.

Figure 2:
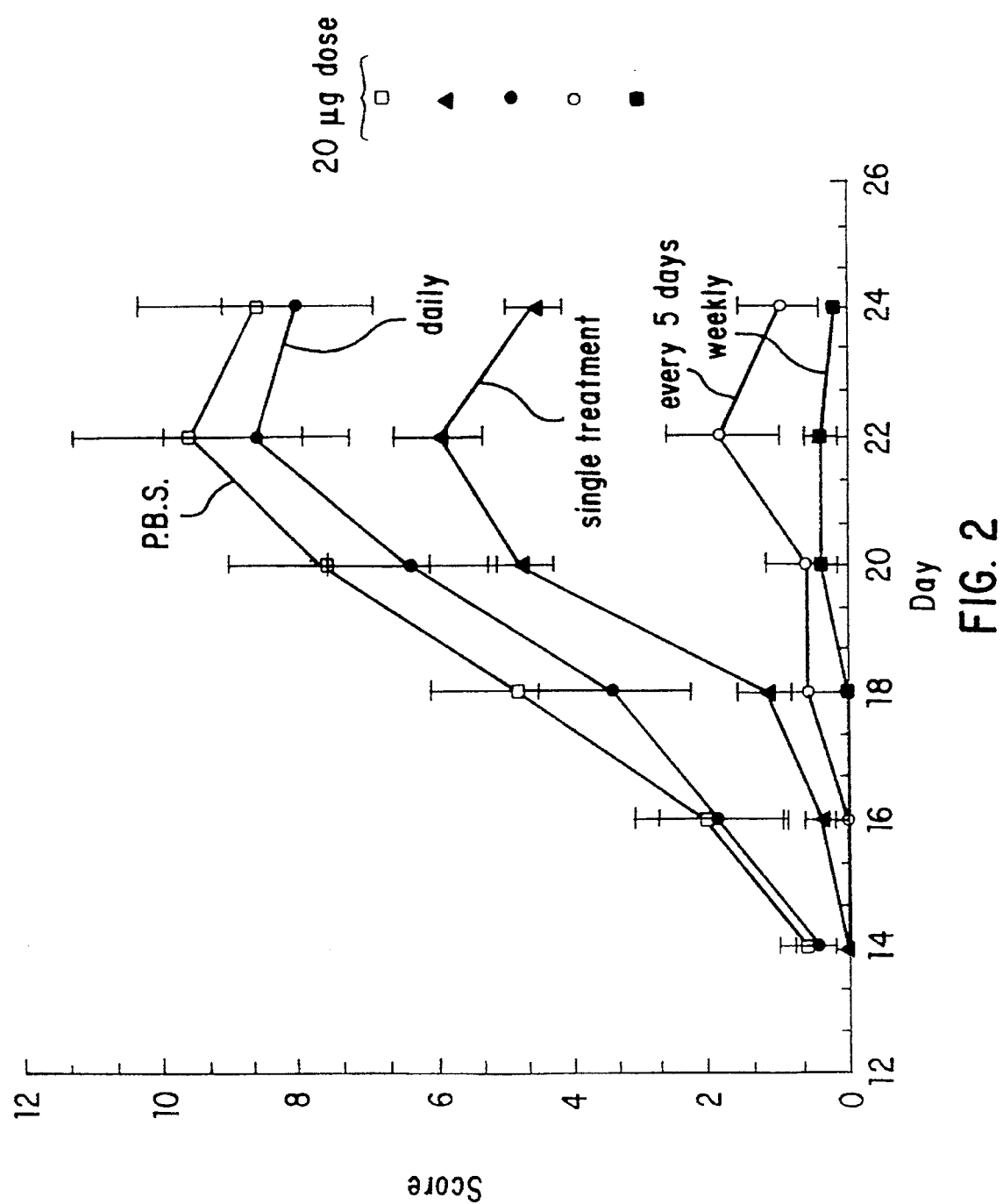

The effect of the 20 µg dose of Fragmin® on the course of AA is shown in FIG. 2: PBS control (□); single treatment on 5th day (▲); daily (574 ); every 5th day (o); weekly (■). It is shown that Fragmin administration both at 5 day intervals and at 7 day intervals inhibits arthritis.

Figure 3:
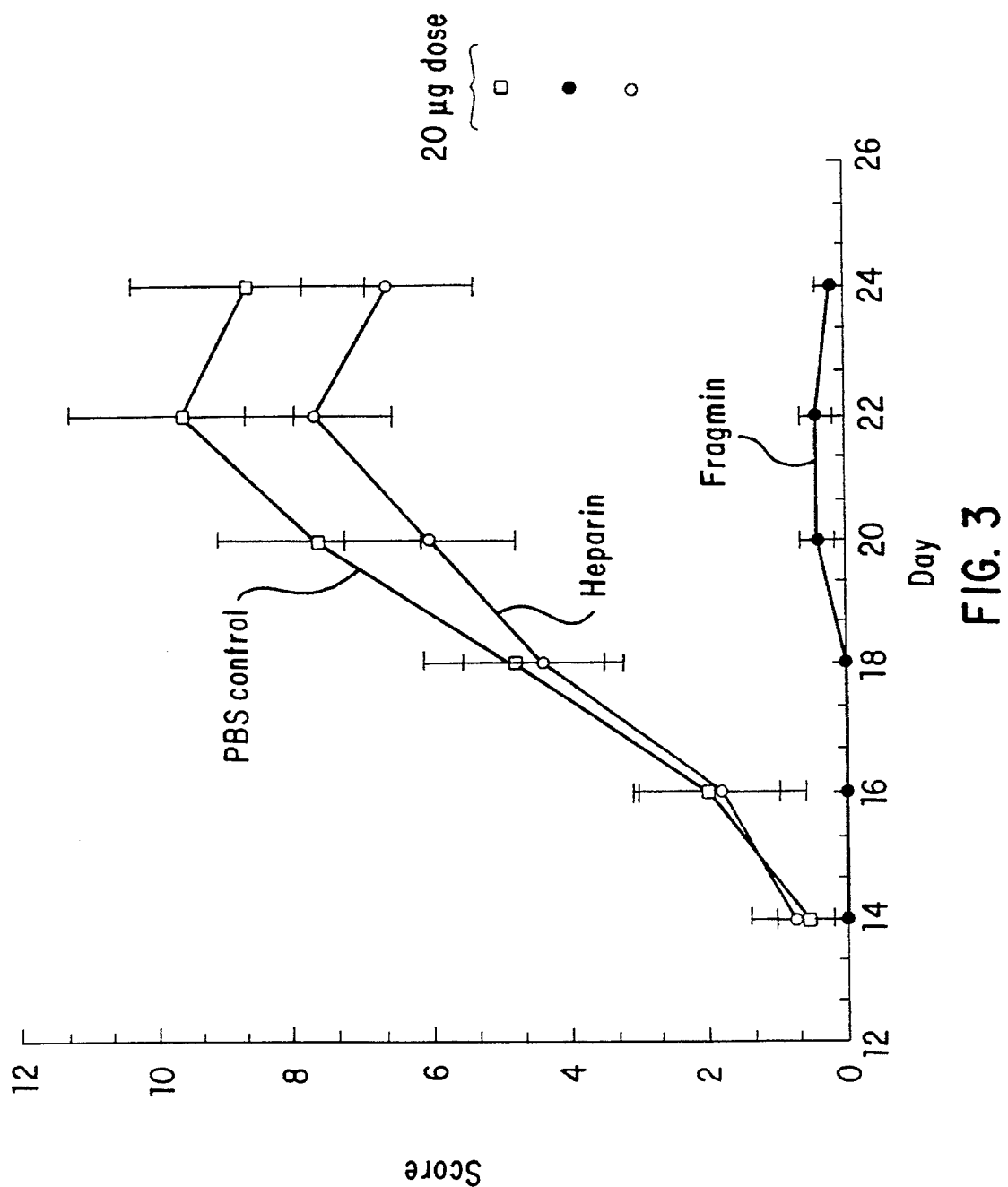

FIG. 3 shows the effect of weekly administration of Fragmin® (batch 38609) as compared to standard heparin on AA. Lewis rats were immunized to induce AA. Beginning on day 5, the rats were inoculated subcutaneously at weekly intervals with a 20 μg dose of Fragmin® (■), heparin (o) or phosphate buffered saline (PBS) control (□). The results show a dramatic difference in potency between Fragmin® and heparin: Fragmin® completely inhibited arthritis, while heparin had no inhibitory effect.

Figure 4:
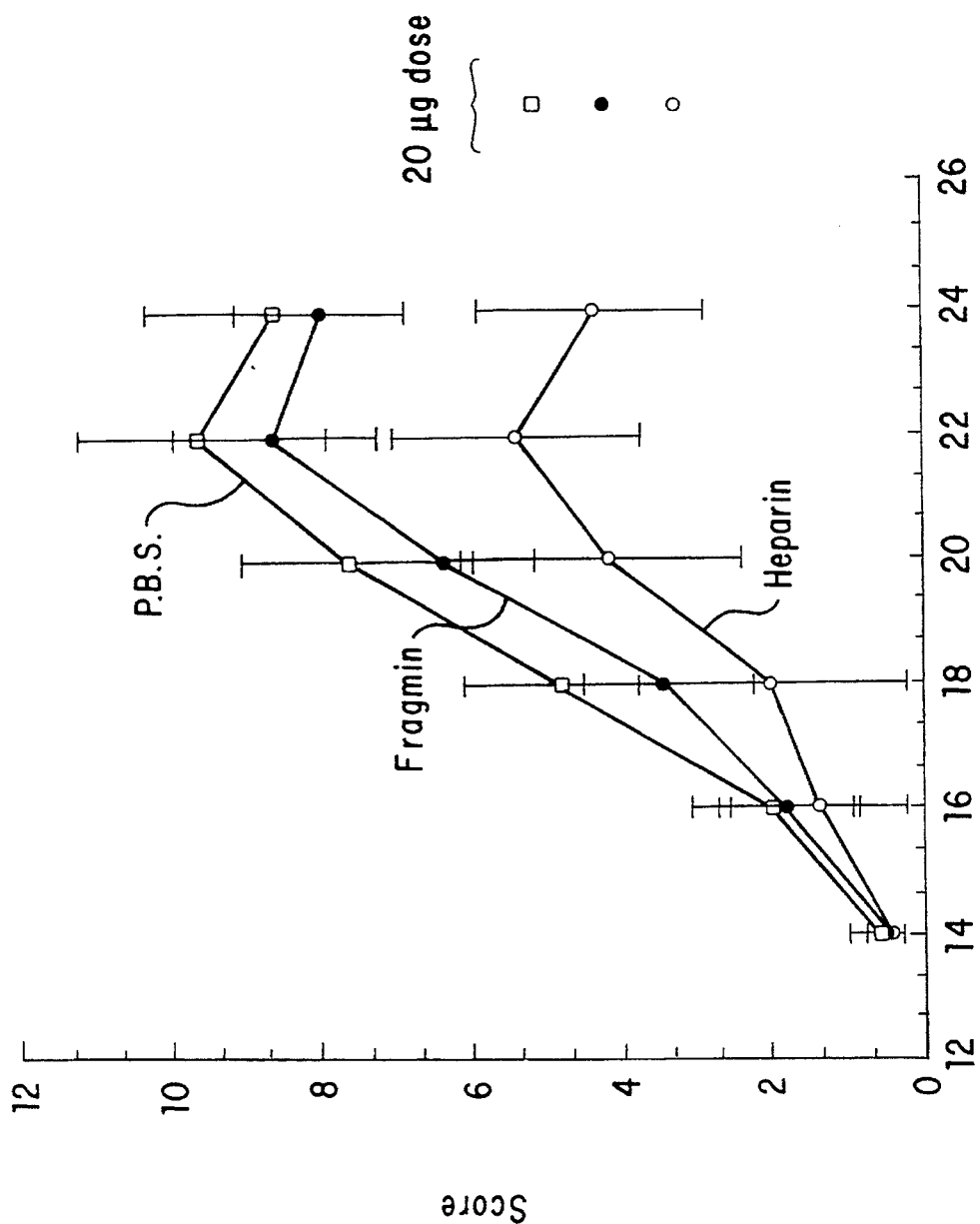

No inhibitory effect on AA was found with daily administration of a 20 μg dose of LMWH, although surprisingly the inhibitory effect of heparin was stronger than that of Fragmin® in daily administration, as shown in (FIG. 4: Fragmin® (batch 38609)(●), heparin (o), PBS control (□)).

Figure 5:
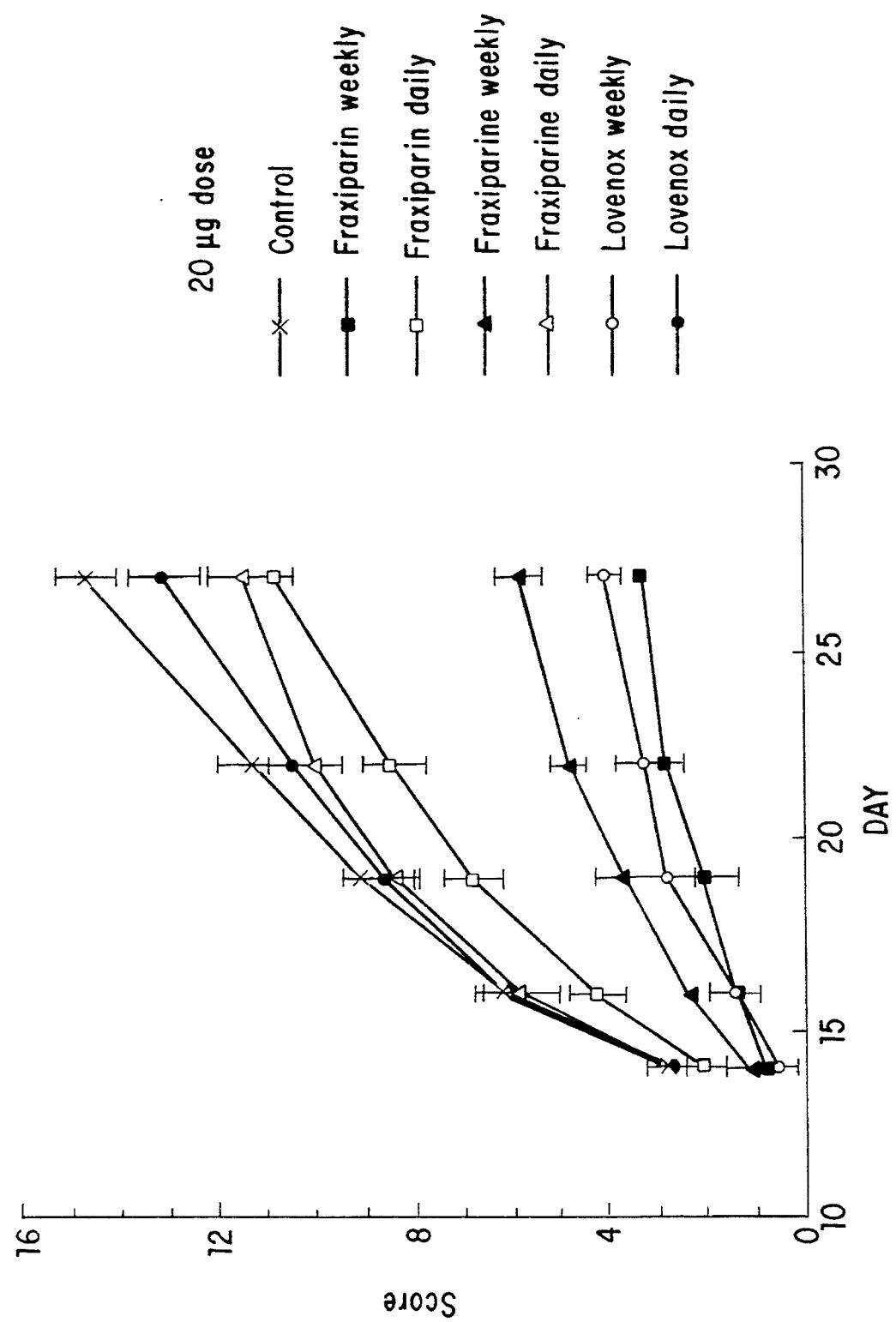

A similar inhibitory effect was observed with several other LMWHs administered to Lewis rats immunized to induce AA. FIG. 5 shows the results of the injection of a 20 μg dose of Fraxiparin® (daily (□); weekly (■)); Fraxiparine® (daily (△); weekly (▲)), Lovenox®/Clexane® (daily (●); weekly (o)), and PBS control (x). All the three LMWHs of different types and sources showed a marked inhibition of arthritis, when administered weekly, but not daily.

5.8. EXAMPLE 8: Treatment With LMWH Prevents Rejection of Allografts

Figure 6:
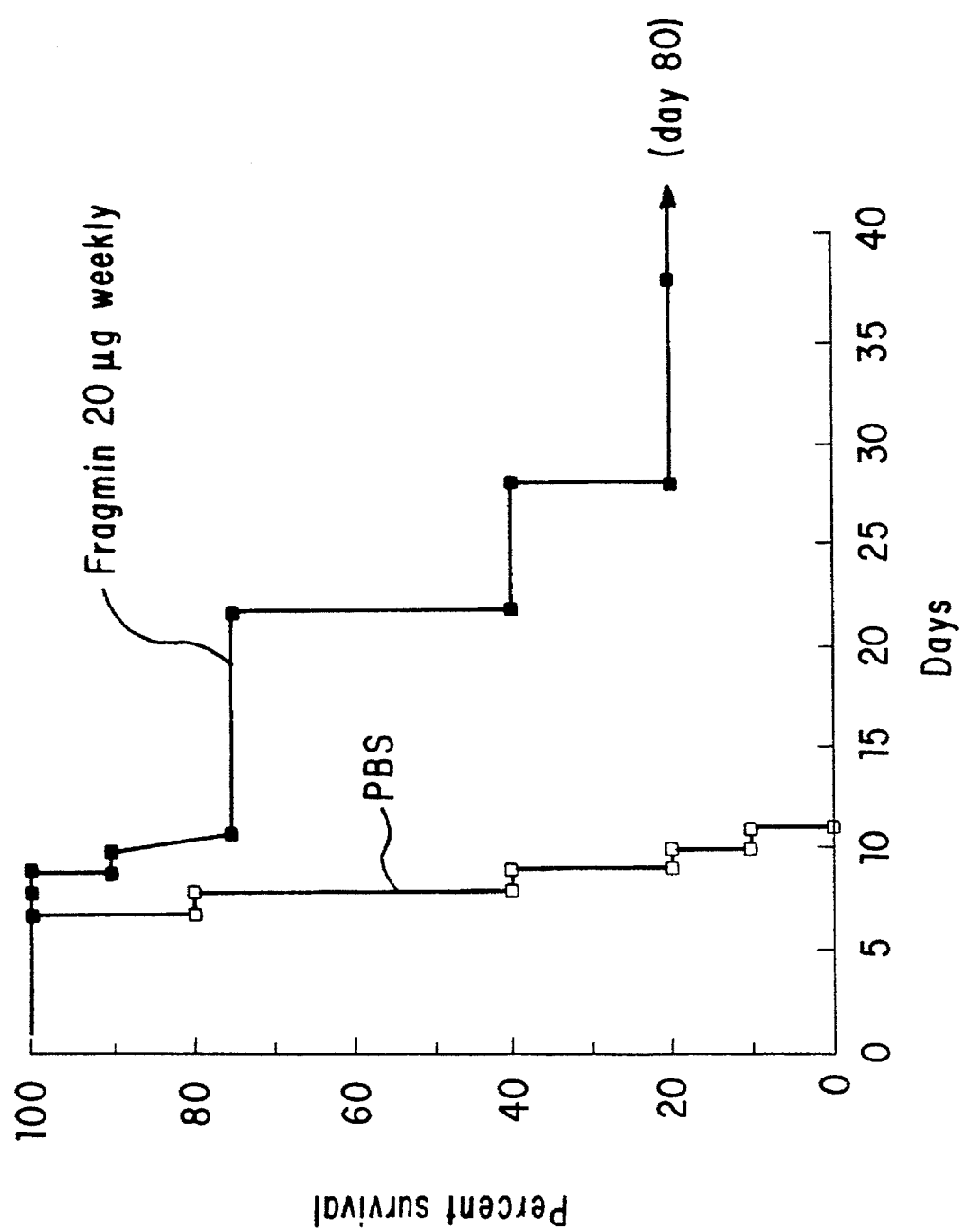

Wistar rats were subjected to allogeneic BN heart transplant (Ono, K. and Linsay, E.S., *J. Thorac. Cardiovasc. Surg.* (1969) 45:225–229). From the day before transplantation, the rats were injected subcutaneously at 7 day intervals with 20 μg of Fragmin® or PBS control (FIG. 6, ■ and □, respectively) and scored for survival. The day of rejection was determined as the day the transplanted heart stopped beating, assayed by palpation of the abdomen. FIG. 6 shows that the rats treated with the weekly dose of LMWH had a markedly increased survival of the heart allografts.

5.9. EXAMPLE 9: Biological Effect of LMWH On Insulin Dependent Diabetes Mellitus (IDDM) of NOD Mice Mice of the NOD strain spontaneously develop a form of type I insulin dependent diabetes mellitus (IDDM) that is the accepted model for human IDDM (Castano, L. and Eisenbarth, G.S., *Annu. Rev. Immunol.* (1990) 8:647–679). The disease begins at 4–5 weeks of age by the appearance of inflammation of the pancreatic islets, insulitis. The insulitis progressively damages the insulin-producing beta cells which are sensitive to damage by TNF-α. At about 4–5 months of age, a sufficient number of beta cells are destroyed so that diabetes becomes overt.

Figure 7:
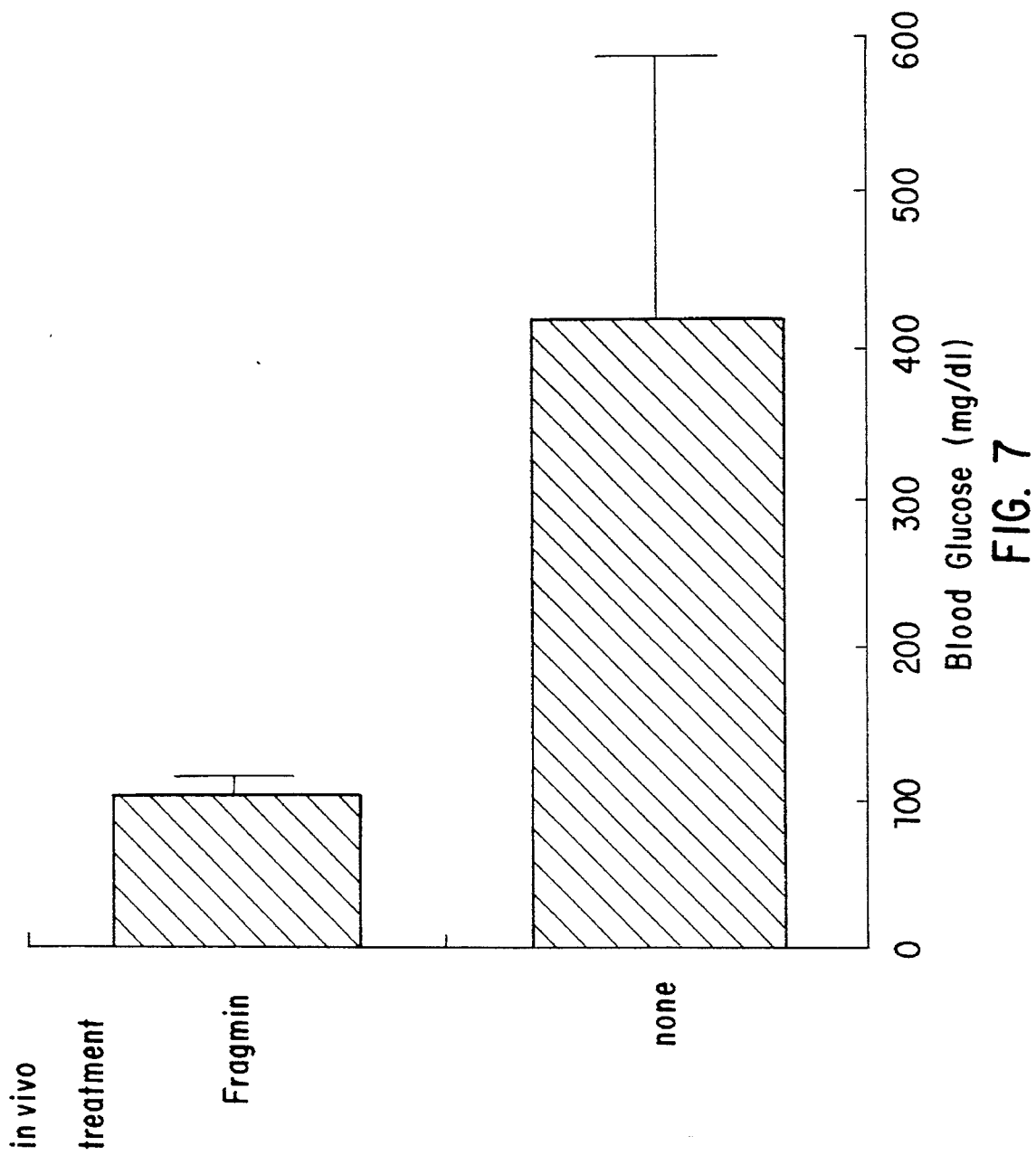

To test whether treatment with LMWH could affect the IDDM process, a group of 10 female NOD mice was treated with weekly subcutaneous injections of 5 μg per mouse of Fragmin® (batch 38609), the dose determined to represent 12 mouse units per kg. A group of 10 control mice were treated with injections of saline. At the age of 5 months all the mice were bled to determine the development of IDDM using a standard procedure (Elias, D. et al., *Proc. Natl. Acad. Sci. U.S.A.* (1990) 87:1576–1580). FIG. 7 shows that the control mice ("none") had abnormal blood glucose (400 mg/dl). In contrast the mice treated with LMWH had a normal blood glucose (100 mg/dl). Thus treatment with LMWH can indeed cure the IDDM process.

5.10. EXAMPLE 10: LMWH Treatment of Human DTH

Figure 8:
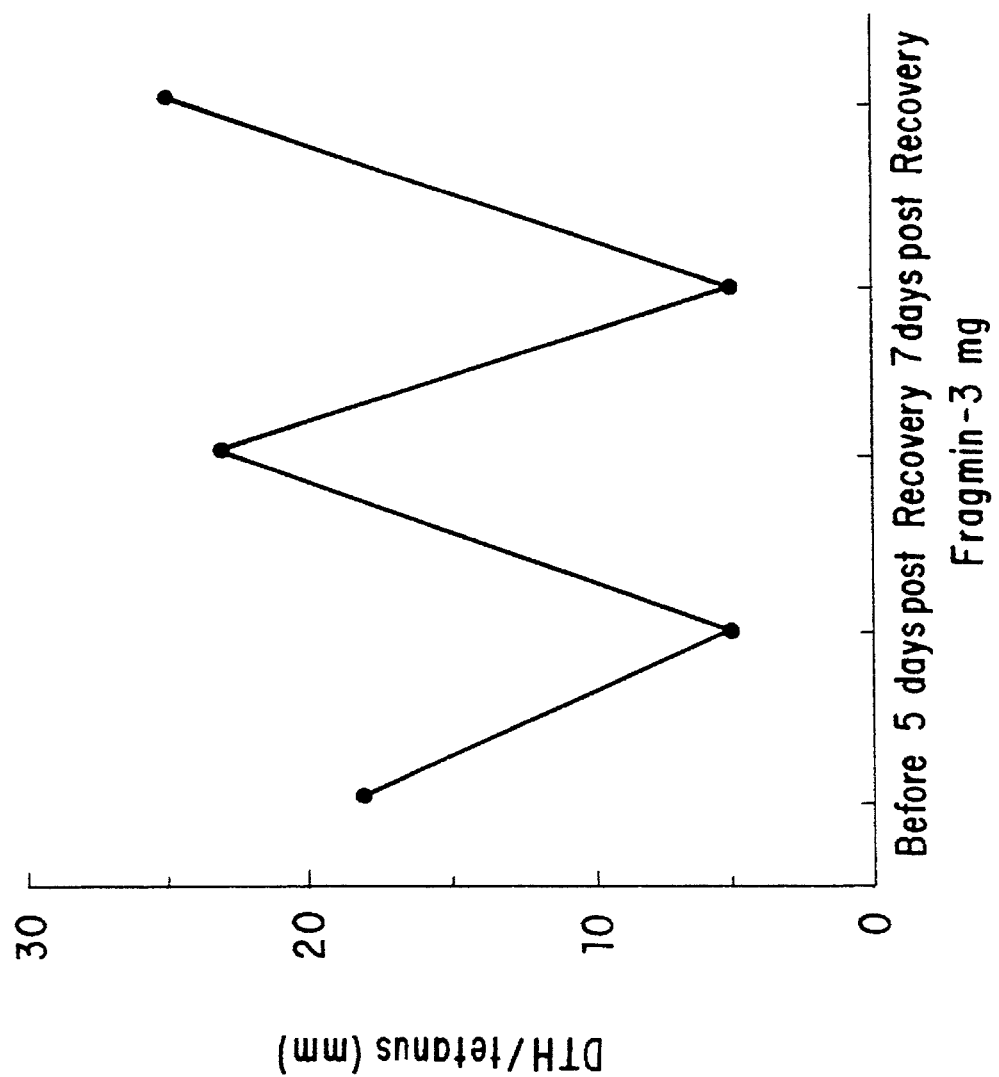

FIG. 8 shows an experiment in which a 40 year old male volunteer weighing 85 kg was tested for DTH reactivity to tetanus antigen (Merieux skin test applicator). About 18 mm of induration was measured at 24 and 48 hours. The volunteer was then treated with a subcutaneous injection of Fragmin® (batch 38609) 3 mg. Five days later the volunteer was again tested for his DTH response to tetanus and the induration was inhibited to about 5 mm. The volunteer was tested again for DTH 3 weeks later ("Recovery") and the test showed positive reactivity (23 mm of induration at 24 and 48 hours). The volunteer was then treated with Fragmin® as before and the DTH reactivity was measured again 7 days later ("7 days post"). Again the DTH was inhibited to about 5 mm of induration. Recovery of DTH again was found 3 weeks later. Thus, LMWH at a dose of less than 5 mg can inhibit DTH in humans at treatment intervals of 5 and 7 days.

It should be apparent to those skilled in the art that other compositions and methods not specifically disclosed in the instant specification are, nevertheless, contemplated thereby. Such other compositions and methods are considered to be within the scope and spirit of the present invention. Hence, the invention should not be limited by the description of the specific embodiments disclosed herein but only by the following claims.

What is claimed is:

1. A method of treating a subject suffering from a pathological process involving induction of Tumor Necrosis Factor alpha (TNF-α) secretion comprising administering to a subject in need of such treatment a pharmaceutical composition comprising
   (a) a pharmaceutically acceptable carrier and
   (b) a dose unit of low molecular weight heparin (LMWH) greater than or equal to the minimum effective dose per kg body weight of a human subject and less than or equal to the maximum effective dose per kg body weight of a human subject wherein
      (i) the minimum effective dose is one-twelfth the lowest amount of said LMWH per kg of body weight that when administered to mice at intervals of about 5–8 days causes at least 50% inhibition of in vitro TNF-α secretion by resting T cells and/or macrophages from said mice in response to T cell-specific antigens, mitogens, macrophage activators, disrupted extracellular matrix (dECM), laminin, or fibronectin; and
      (ii) the maximum effective dose is one-twelfth the greatest amount of said LMWH per kg of body weight that when administered to mice at intervals of about 5–8 days causes at least 50% inhibition of in vitro TNF-α secretion by resting T cells and/or macrophages from said mice in response to T cell-specific antigens, mitogens, macrophage activators, disrupted extracellular matrix (dECM), laminin, or fibronectin, wherein said administering to a subject is carried out at intervals of about 5–8 days, and wherein the molecular weight of LMWH is from about 3,000 to about 6,000.

2. A method of treating a subject suffering from a pathological process involving induction of Tumor Necrosis Factor alpha (TNF-α) secretion comprising administering to a subject in need of such treatment a pharmaceutical composition comprising
   (a) a pharmaceutically acceptable carrier and
   (b) a dose unit of low molecular weight heparin (LMWH) greater than or equal to the minimum effective dose per kg body weight of a human subject and less than or equal to the maximum effective dose per kg body weight of a human subject wherein
(i) the minimum effective dose is one-twelfth the lowest amount of said LMWH per kg of body weight that causes at least 50% inhibition of an experimental delayed type hypersensitivity (DTH) reaction of pre-sensitized mice to an applied antigen as evidenced by a reduction in the induration observed after said antigen is applied to the skin five to seven days after the administration of said LMWH relative to the induration observed after said antigen is applied to the skin in the absence of or after recovery from the administration of said LMWH; and
(ii) the maximum effective dose is one-twelfth the greatest amount of said LMWH per kg of body weight that causes at least 50% inhibition of an experimental DTH reaction of pre-sensitized mice to an applied antigen as evidenced by a reduction in the induration observed after said antigen is applied to the skin five to seven days after the administration of said LMWH relative to the induration observed after said antigen is applied to the skin in the absence of or after recovery from the administration of said LMWH;

wherein said administering to a subject is carried out at intervals of about 5–8 days, and wherein the molecular weight of LMWH is from about 3,000 to about 6,000.

3. The method of claim 1 or 2 wherein said interval between administrations is seven days.

4. The method of claim 1 or 2 wherein said subject is in need of treatment for inflammatory bowel disease or rheumatic disease.

5. The method of claim 1 or 2 wherein said subject is in need or treatment for allergy or chronic inflammatory disease.

6. The method of claim 1 or 2 wherein said subject is in need of said treatment for an allergic reaction.

* * * * *